United States Patent
Noel et al.

(10) Patent No.: US 11,717,541 B2
(45) Date of Patent: Aug. 8, 2023

(54) BIOPOLYMER COMPOSITIONS FOR THE TREATMENT AND PREVENTION OF GASTRIC ULCERS

(71) Applicant: SIDR, LLC, Dover, DE (US)

(72) Inventors: Scott P. Noel, Germantown, TN (US); William Brian Austin, Germantown, TN (US); Alex Greene, Germantown, TN (US); John Kirk Shumpert, Germantown, TN (US)

(73) Assignee: SIDR, LLC, Dover, DE (US)

(*) Notice: Subject to any disclaimer, the term of this patent is extended or adjusted under 35 U.S.C. 154(b) by 140 days.

(21) Appl. No.: 17/220,455

(22) Filed: Apr. 1, 2021

(65) Prior Publication Data

US 2021/0220410 A1    Jul. 22, 2021

Related U.S. Application Data

(63) Continuation of application No. 16/489,647, filed as application No. PCT/US2018/020683 on Mar. 2, 2018, now Pat. No. 10,987,383.

(60) Provisional application No. 62/467,000, filed on Mar. 3, 2017.

(51) Int. Cl.

| | |
|---|---|
| *A61K 36/185* | (2006.01) |
| *A61K 35/644* | (2015.01) |
| *A23K 20/163* | (2016.01) |
| *A23K 50/20* | (2016.01) |
| *A23K 10/30* | (2016.01) |
| *A61P 1/04* | (2006.01) |
| *A61K 9/00* | (2006.01) |
| *A61K 31/722* | (2006.01) |
| *A61K 31/733* | (2006.01) |
| *A61K 36/61* | (2006.01) |
| *A61K 45/06* | (2006.01) |

(52) U.S. Cl.
CPC ............ *A61K 35/644* (2013.01); *A23K 10/30* (2016.05); *A23K 20/163* (2016.05); *A23K 50/20* (2016.05); *A61K 9/0053* (2013.01); *A61K 9/0056* (2013.01); *A61K 31/722* (2013.01); *A61K 31/733* (2013.01); *A61K 36/185* (2013.01); *A61K 36/61* (2013.01); *A61K 45/06* (2013.01); *A61P 1/04* (2018.01)

(58) Field of Classification Search
CPC .................................................... A61K 36/185
See application file for complete search history.

(56) References Cited

U.S. PATENT DOCUMENTS

| | | | |
|---|---|---|---|
| 7,226,590 B2 | 6/2007 | Chilcott et al. | |
| 10,987,383 B2 | 4/2021 | Noel et al. | |
| 11,116,809 B2 | 9/2021 | Noel et al. | |
| 2008/0050455 A1* | 2/2008 | Smith | ........... A61P 1/04 424/692 |
| 2011/0038945 A1 | 2/2011 | Gear | |
| 2016/0367606 A1 | 12/2016 | Petito | |
| 2020/0129564 A1 | 4/2020 | Noel et al. | |

FOREIGN PATENT DOCUMENTS

| | | |
|---|---|---|
| WO | 2002096451 A1 | 12/2002 |
| WO | 2017040629 A1 | 3/2017 |

OTHER PUBLICATIONS

Aiko, Dj, "Health Benefits of Slippery Elm Bark," 2013, retrieved from the Internet on Apr. 4, 2018, <URL: https://suziqi.nl/2013/03/21/health-benefits-of-slippery-elm-bark/>.

English bibliographic information for Manuka Red Ginseng Co. Ltd., KR 10-2015-064829 A, 2015.

International Search Report and Written Opinion dated Apr. 24, 2018 in corresponding International PCT Patent Application No. PCT/US2018/020683 (13 pages).

* cited by examiner

*Primary Examiner* — Rosanne Kosson

(74) *Attorney, Agent, or Firm* — Melissa Hunter-Ensor; Nathan Hsu; Greenberg Traurig, LLP

(57) ABSTRACT

The invention provides compositions comprising chitosan, manuka honey and one or more additional components that promotes digestive health (e.g., inulin, probiotics) for the treatment and prevention of gastric ulcers (esophageal, stomach, or duodenum) in a mammal (e.g., equine).

5 Claims, No Drawings

BIOPOLYMER COMPOSITIONS FOR THE TREATMENT AND PREVENTION OF GASTRIC ULCERS

CROSS-REFERENCE TO RELATED APPLICATIONS

This application is a continuation of U.S. Utility application Ser. No. 16/489,647, filed Aug. 28, 2019, which is a U.S. national phase application, pursuant to 35 U.S.C. § 371, of PCT International Application Ser. No.: PCT/US2018/020683, filed Mar. 2, 2018, designating the United States and published in English, which claims the benefit of and priority to U.S. Provisional Application Ser. No. 62/467,000, filed Mar. 3, 2017, all of which are incorporated herein by reference in its entirety.

BACKGROUND OF THE INVENTION

In humans, gastric ulcers, often referred to as peptic ulcers, are painful sores along the lining of the stomach or the duodenum, the first section of the small intestine. Ulcers may be caused by an imbalance in the digestive fluids present in the stomach. Several factors can increase the prevalence of gastric ulcers including the use of NSAIDs, alcohol, or tobacco, radiation, serious illness, illness causing excess acid production or infection from *Helicobacter pylori*. Symptoms of gastric distress related to gastric ulcers include pain, heartburn, and nausea. Without treatment, gastric ulcers in humans may lead to weight loss, internal bleeding, perforation of the lining of the stomach, or swelling that could create gastric obstruction.

Gastric ulcers are common in other mammals as well, including horses. Horses with ulcers may develop a debilitating condition requiring intervention. EGUS, Equine Gastric Ulcer Syndrome, is a designation used to describe many aspects of this complicated condition. It is estimated that 25-50% of foals, and 60-90% of all horses will experience gastric ulcers, and this number climbs when looking at horses in training, such as thoroughbreds, hunters, jumpers, and eventers.

The equine stomach is segregated into two sections, the non-glandular region and the glandular region. The non-glandular section makes up approximately one-third of the equine stomach, with the glandular region accounting for the remaining two-thirds of the stomach. The non-glandular region lacks glands and is lined with stratified squamous epithelium, whereas the glandular region contains glands that secrete hydrochloric acid, pepsin, bicarbonate, and mucus. Many equine gastric ulcers are present in the non-glandular region. Horses that receive NSAIDs or that have certain medical conditions may present with ulcers in the glandular region. Additionally, foals and adult horses may have ulcers in the duodenum. The glandular region of the equine stomach constantly secretes hydrochloric acid in variable volumes, with or without the presence of feed in the stomach. Adult horses secrete, on average 1.5 liters of gastric fluids per hour, representing approximately 60 mmoles of hydrochloric acid per hour. The pH of the equine stomach is variable depending on section, but may become overly acidic if not managed. Lifestyle and diet, particularly with respect to foals and adult horses in training, may exacerbate this acidity, predisposing the horse to ulcers.

Ulcers may result from imbalances in hydrochloric acid, pepsin, bile acids, and organic acids present in gastric fluids and protective elements, such as bicarbonate and mucus. Due to the structural differences in various sections of the equine stomach, the mode of action in ulcer development is varied due to various concentrations of underlying gastric fluid components. The severity of ulceration in the stomach is due to the degree and length of time of exposure. Factors thought to influence the onset of an ulcer-causing fluid imbalance are fasting (feed deprivation), stress, reduced gastric motility, diet, and desquamation. Feed deprivation or irregular feeding has been shown to reduce stomach pH, which could play a direct role in the development of equine stomach ulcers. In addition to irregular feeding, stress induced imbalances are particular present in horses in training. Exercise and stress create prolonged exposure to gastric fluids, and a reduction in gastric motility. Delayed gastric emptying (motility) has been associated with ulcer formation. Furthermore, equine diet, particularly that of a horse in training, has been linked to the presence of gastric ulcers.

Horses in training are often fed diets high in fermentable carbohydrates. These carbohydrates, when fermented, create a byproduct of volatile fatty acids (VFA). VFAs penetrate the mucosal lining of the stomach and are linked to cell damage, inflammation, and ulceration. Horses have been found to have significant levels of VFAs present when in training. Diagnosing gastric ulcers of the equine stomach is typically confirmed through endoscopic examination. There are, however, clinical signs that present depending on whether the horse is a foal or adult. The foal may present with colic, poor appetite, diarrhea, excess salivation (ptyalism), grinding of teeth (bruxism), intermittent nursing, or dorsal recumbency. Adult horses with ulcers often present with lack of appetite, changes in demeanor, decreased performance, reluctance to train, reduced body condition, rough hair coat, weight loss, excessive recumbency, and low-grade colic.

Current treatments include changes to diet, lifestyle, or pharmaceutical management. Pharmaceutical management may be administered through Omeprazole paste (GastroGard, Merial Limited). Omeprazole is an acid pump inhibitor that inhibits the production of stomach acid. Omeprazole paste is the only FDA cleared pharmaceutical for the treatment of equine gastric ulcers. Full doses are administered for the treatment of existing gastric ulcers, while half doses are typically used for the prevention of gastric ulcers. Long-term use of Omeprazole is not, however, without controversy; as long-term exposure is thought to increase the risk of fracture, particularly in horses in training. Accordingly, improved compositions and methods for treating equine ulcers are urgently required.

SUMMARY OF THE INVENTION

The invention provides compositions comprising chitosan, manuka honey and one or more additional components that promotes digestive health (e.g., inulin, probiotics) for the treatment and prevention of gastric ulcers (e.g., esophageal, stomach, or duodenum) in a mammal (e.g., equine).

In one aspect, the invention features a composition for the treatment or prevention of an ulcer containing any of the ingredients in Table 1 or manuka honey and a biopolymer that is any one or more of chitosan, cellulose, collagen, and alginate in a form suitable for oral administration. In one embodiment, the composition further contains slippery elm. In another embodiment, the composition further contains inulin or another probiotic. In another embodiment, the composition further contains aloe water and/or aloe vera. In another embodiment, the composition further contains one or more acids selected from the group consisting of ascorbic acid, citric acid, malic acid, apple cider vinegar, rice vinegar or other acetic acids or vinegars. In another embodiment, the composition further contains lecithin. In another embodiment, the composition further contains a flavoring selected from the group consisting of apple, apple butter, apple pectin, peppermint, and citrus. In another embodiment, the composition further contains a plant-based composition selected from the group consisting of a pomace, powder, liquid, concentrate, and a lyophilized component. In another embodiment, the composition further contains a fungal composition (e.g., derived from a mushroom, such as schizophyllan) or a plant-based composition derived from a fruit (e.g., banana, berry, apple, or citrus fruit, such as orange, lemon, lime), vegetable (e.g., beet, beetroot, other root-based flora), grain or herb. In one embodiment, the plant-based composition has anti-inflammatory activity. In another embodiment, the composition further containing a preservative that is ascorbic acid, potassium sorbate or citric acid. In another embodiment, the composition further containing a polyol selected from the group consisting of glycerol, glycerine, glycerin, maltitol, sorbitol, xylitol, erythritol, or isomalt. In another embodiment, the chitosan is present in the range of 0.00001 to 10 wt %, from 0.00001 to 5 wt %, or from 0.00001 to 3 wt %. In another embodiment, the manuka honey is present in the range of 0.00001 to 10 wt %, from 0.00001 to 5 wt %, or from 0.00001 to 3 wt %. In another embodiment, the lecithin is present in the range of 0.00001 to 25 wt %, preferably from 0.00001 to 10 wt %. In another embodiment, acids are present individually in the range of 0.00001 to 10 wt %, from 0.00001 to 5 wt %, from 0.00001 to 3 wt %, and collectively not more than 5% of the composition. In another embodiment, the composition is a liquid, gel, semi-liquid, semi-solid, paste, or solid form. In another embodiment, water makes up the balance of the solution, and represents no less than 60 wt % of the entire solution. In another embodiment, the composition is formulated for delivery through a syringe, formed into a powder, feed, feed additive, or treat. In another embodiment, the composition further contains a soluble or insoluble nano-particulate. In another embodiment, the nano-particulate is Silver, Magnesium, Copper, Arsenic, Zinc, Tellurium, or Mercury. In another embodiment, the composition contains a soluble or insoluble antimicrobial, antifungal, or antibacterial agents.

In another aspect, the invention features a pharmaceutical composition containing the composition of a previous aspect.

In another aspect, the invention features a method for treating digestive distress in a mammal, the method involving administering to the mammal an effective amount of a composition of any previous aspect.

In another aspect, the invention features a method for treating or preventing a gastric ulcer, the method involving administering to the animal an effective amount of a composition of any previous aspect. In one embodiment, the mammal has Equine Gastric Ulcer Syndrome (EGUS).

In another aspect, the invention features a method for maintaining a healthy digestive environment, the method involving administering to the animal an effective amount of a composition of any previous aspect.

In various embodiments of the above aspects, the mammal is an equine, bovine, ovine, feline, or canine.

Definitions

By "alginate" is meant the sodium salt of alginic acid. In particular embodiments, alginic acid refers to a linear copolymer with homopolymeric blocks of (1-4)-linked 1-D-mannuronate (M) and its C-5 epimer .alpha.-L-guluronate (G) residues, respectively, covalently linked together in different sequences or blocks.

By "chitosan" is meant a chitin-derived polymer that is at least 20% deacetylated. Preferably, chitosan is at least about 50% deacetylated. Chitin is a linear polysaccharide consisting of (1-4)-linked 2-acetamido-2-deoxy-b-D-glucopyranose. Chitosan is a linear polysaccharide consisting of (1-4)-linked 2-amino-2-deoxy-b-D-glucopyranose.

By "acid treated chitosan" is meant chitosan that is solubilized in an acidic solution.

By "collagen" is meant a protein component of an extracellular matrix having a tertiary structure that includes polypeptide chains intertwining to form a collagen triple helix or having a characteristic amino acid composition comprising Gly-X-Y repeat units, or a fragment thereof. Collagens useful in the methods of the invention include any collagen known in the art (e.g., one of collagen type 1-29).

By "composite" is meant a mixture of materials.

By "agent" is meant any small compound, macromolecule, biopolymer, polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "antimicrobial" is meant an agent that inhibits or stabilizes the proliferation or survival of a microbe. In one embodiment, a bacteriostatic agent is an antimicrobial. In other embodiments, any agent that kills a microbe (e.g., bacterium, fungus, virus) is an antimicrobial.

By "anti-inflammatory" is meant an agent that reduces the severity or symptoms of an inflammatory reaction in a tissue.

By "clinician" is meant any healthcare provider. Exemplary clinicians include, but are not limited to, doctors, veterinarians, osteopaths, physician's assistants, emergency medical technicians, medics, nurse practitioners, and nurses.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. In one example, a disease is an ulcer or other wound affecting the gastrointestinal system of a mammal.

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "polymer" is meant a natural or synthetic organic molecule formed by combining smaller molecules in a regular pattern.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "subject" is meant a mammal, including, but not limited to, a human or non-human mammal, such as a bovine, equine, canine, ovine, or feline.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control condition.

DETAILED DESCRIPTION OF THE INVENTION

The invention provides compositions comprising chitosan, manuka honey and one or more additional components that promotes digestive health (e.g., inulin, probiotics) for the treatment and prevention of gastric ulcers (esophageal, stomach, or duodenum) in a mammal (e.g., equine).

The present invention approaches ulcer treatment from a wound care perspective, whether protecting and preventing ulcers or treating existing ulcers.

A nutraceutical composition of the invention may be used temporarily (e.g., for a few days, weeks) or may be used on an on-going basis (e.g., months, years) as a permanent daily use supplement, or may be used to treat an acute condition following the onset or suspicion that ulcer symptoms are present.

Equine Digestive Health

Ulceratic lesions in the mucosal lining of the digestive tract are common in equines (e.g., horses) used for recreation, commercial and/or agricultural purposes. In particular, many competitive activities, including racing, dressage, showjumping, endurance events and western performance, lead to ulcers and related symptoms in horses participating in these activities. Depending on the intensity of training, the prevalence of gastric ulcers in horses can affect from 10% to 90% of participating horses. Apart from exercise, many factors contribute to the development of ulcers, for example, transport to and from show grounds, stall confinement in unfamiliar surroundings, grain-based diets, ingestion of anti-inflammatory agents, and/or irregular feeding schedules.

The symptoms of ulcers in affected animals can be subtle and may include irritability and changes in attitude and behavior, poor appetite, and decreased performance and energy. These symptoms may also be exhibited with other symptoms, such as lethargy; musculo/skeletal discomfort and pain; decline or deterioration in body condition and/or appearance (dull hair coat); weight loss; alterations in eating or drinking patterns; resistance to grooming; reluctance or refusal to performing certain tasks; and behavior indicating discomfort, such as pawing or laying down excessively. Still other signs that may correlate with ulcers in the animal include sensitivity in the flank area and girthiness; cribbing (windsucking); wood-chewing; and weaving in the stall, an (atypical) unwillingness to work or cooperate, and resistance under saddle. Foals afflicted with an ulcer may also grind their teeth or lay on their backs. Once an ulcer is suspected or determined in a non-human animal, such as horses, ponies, camels, donkeys, or mules, particularly, horses, the methods of the invention are useful in treating gastric and colonic ulcers and/or the symptoms of such ulcers in the animal.

The invention provides methods directed to treating gastric and/or colonic ulcers and the uncomfortable and often painful discomfort that they cause in both young and adult horses and other non-human animals. The methods are effective in reducing and/or alleviating the ulcers and the symptoms that afflict such animals in need thereof. In particular, the methods are directed to the treatment of ulcers in horses, particularly ulcers of the colon that can lead to blood loss, irritability and poor absorption of nutrients in ulcerated young and adult animals. Treatment and prevention of ulceratic conditions in horses with the methods and compositions of the invention can positively impact and improve the performance of horses that are expected to perform at peak proficiency, including leisure and recreational horses and show horses, especially training and race horses.

Animals (horses) having a history of gastric and/or colonic ulcers may benefit from proactive treatment with the compositions of the invention to decrease or abrogate the chances of developing ulcers or the recurrence of ulceration. During and following a course of treatment with the compositions and methods described herein, an animal being treated can be monitored for a change in its clinical behavior to determine that the gastric and colonic ulceratic conditions are improved, reduced, or eliminated. Preferably, the animal is examined via endoscopy or gastroscopy to confirm improvement and/or healing of ulceratic lesions, and prior to discontinuing therapy with the methods and compositions of the invention. Endoscopic examination involves short-term tranquilization of the animal to reduce stress to the animal from the procedure. Thereafter, an endoscope is inserted through the animal's nostril and guided down the esophagus into the stomach wherein the light and camera on the endoscope's terminus allow observation of the stomach lining. A complete endoscopic evaluation can take about 10 to 20 minutes and is safe for the animal.

Nonlimiting examples of animals affected by gastrointestinal ulcers and treatable by the methods and formulations of the invention particularly include young (foals) and adult equine animals (horses). Other animals that may suffer from ulcers and benefit from treatment and prevention by the methods and compositions described herein include canines, felines, young camels (calves) and adult camels. In addition, young cattle (calves), pigs (piglets), sheep (lambs), goats (kids), horses (foals) and adult animals, including, cattle, steer, bison, buffalo, goats, sheep and rams, may be treated according to the methods of the invention. In some embodiments, a composition of the invention is used to treat a human.

Chitosan

Chitosan is a naturally occurring linear polysaccharide composed of randomly distributed β-(1-4)-2-amino-2-D-glucosamine (deacetylated) and β-(1-4)-2-acetamido-2-D-glucoseamine (acetylated) units. Chitosan is derived from chitin, a naturally occurring polymer. Chitin is a white, hard, inelastic, nitrogenous polysaccharide isolated from fungi, mollusks, or from the exoskeletons of arthropods (e.g., crustaceans, insects). The major procedure for obtaining chitosan is the alkaline deacetylation of chitin with strong alkaline solution. Generally, the raw material is crushed, washed with water or detergent, and ground into small pieces. After grinding, the raw material is treated with alkali and acid to isolate the polymer from the raw crushed material. The polymer is then deacetylated by treatment with alkali. Chitin and chitosan differ in their degrees of deacetylation (DDA). Chitin has a degree of deacetylation of 0% while pure chitosan has a degree of deacetylation of 100%. Typically, when the degree of deacetylation is greater than about 50% the polymer is referred to as chitosan.

Chitosan is a cationic weak base that is substantially insoluble in water and organic solvents. Typically, chitosan is fairly soluble in dilute acid solutions, such as acetic, citric, oxalic, proprionic, ascorbic, hydrochloric, formic, and lactic acids, as well as other organic and inorganic acids. Chitosan's charge gives it bioadhesive properties that allow it to bind to negatively charged surfaces, such as biological tissues present in a gastrointestinal tract of an animal.

In the body chitosan is degraded by lysozyme, N-acetyl-o-glucosaminidase and lipases. Lysozyme degrades chitosan by cleaving the glycosidic bonds between the repeating chitosan units. The byproducts of chitosan degradation are saccharides and glucosamines that are gradually absorbed by the body.

This biopolymer material has been used medically, and is valued for its biocompatibility, degradation and absorption properties, hemostatic properties, and for promoting the healing process in damaged tissues. Chitosan has also been linked in scientific literature as being antimicrobial, bacteriostatic, anti-inflammatory, and for reducing itching. Chitosan has been used as coating, a composition binder, and as an active ingredient in pharmaceutical or, ceutical applications.

Collagen

Collagen is the most abundant structural protein in the body, existing as the foremost component of the extracellular matrix (ECM). Most types of collagen contain a unique tertiary structure that includes three individual right-handed helical polypeptide chains intertwining to form a left-handed helix. Collagen has a characteristic amino acid composition comprised of Gly-X-Y repeat units. Collagen is used in a variety of medical applications including hemostatic materials, biocompatible coatings, drug delivery and tissue engineering. Collagen-based biomaterials are also used in soft-tissue engineering and repair. In the past two decades, a multitude of medical products composed of collagen have been approved by the FDA, and many are available as commercial products, including collagen-based corneal shields, anti-infectious catheters, tissue sealants, hemostatic sponges, and topical wound dressing products. Collagen is also used as a tissue engineering substrate for skin, bone, and blood vessel replacement.

Healing Agents

The invention provides pharmaceutical and/or nutraceutical compositions comprising a biopolymer (e.g., chitin, chitosan, collagen, cellulose, alginate, dextrose) and one or more natural healing agents, including but not limited to manuka honey, and optionally comprising one or more of herbal supplements, probiotics, acids, fruits, vegetables, plants (flora), preservatives, polyols, medicaments, antimicrobial additives, antibacterial additives, antifungal additives, or nano-particles. The current embodiment may be provided as a liquid or solid, in the form of powder, hydrogel, paste, pellets, or larger solid compositions.

The invention provides a chitosan solution with varying viscosity comprising natural healing agents, such as manuka honey. Manuka honey is a highly viscous type of honey that has medical applications, as well as antimicrobial properties.

In particular embodiments, a chitosan composition described herein comprises an herbal supplements, including but not limited to slippery elm (*Ulmus fulva*). Slippery elm is useful in the treatment of gastric ulcers. Slippery elm is an herbal supplement derived from the inner bark of the Slippery Elm tree. This herbal supplement is high in mucilage, which becomes a thick gel when in solution and can be used to lubricate and protect wounds, boils, ulcers, and other sores on the body. Further, slippery elm can be used to coat the lining of the stomach to protect and soothe irritations present in the stomach. The inner bark of the Slippery Elm tree is typically dried, through lyophilization or another method, and ground into a powder (dried elm powder), which can be added to a composition of the invention.

In particular embodiments, a chitosan composition described herein comprises a probiotic. Probiotics useful in a composition of the invention, including but not limited to inulin may be added to a composition of the invention to support digestive health. Inulin is a probiotic fiber that not only supports digestive health, but that also inhibits ulcer formation by supporting vitamin absorption, inhibiting certain undesirable bacterial species in the gut, and supporting healthy motility.

In particular embodiments, a chitosan composition described herein comprises one or more acids including, but not limited to, acetic or citric acid, which may be used as a solvent, preservative, flavoring, etc. Acids may be used, for example, as a solvent to dissolve a biopolymer of the invention. In one embodiment a polymer that is present in powder form is dissolved in a liquid solution with varying viscosity. This may be performed by pouring a known mass of biopolymer component together with an acid solvent solution; and mixing until the powder biopolymer is fully dissolved into a liquid solution. Other agents may be added to solution. Depending on viscosity, it may be necessary to apply negative pressure (a vacuum) to the resulting solution prior to filling the container of choice (bottle, tube, syringe, etc.). Further, acids may be used as a preservative to prevent spoilage of the resulting solution, and to maintain or increase shelf life. Acids, such as citric or malic acid, may also be used to affect the flavor profile of the resulting solution as well.

In particular embodiments, a chitosan composition described herein comprises lecithin. Lecithin is the common name for a fat called phosphatidylchoilne. Lecithin upon entering the stomach, breaks down into a mixture of phospholipids that bind to the lining of stomach, thereby providing a protective barrier. Further, lecithin is known to strengthen the mucosa of the stomach lining by interacting with the lining at a cellular level. Additionally, lecithin has been shown to reduce stress and anxiety in horses in training, a known cause of increased prevalence of ulcers.

In particular embodiments, a chitosan composition described herein comprises one or more natural and/or synthetic flavorings to create a palatable nutraceutical. Animals, in particular, are unlikely to show willingness to consume a nutraceutical unless it is flavored in a manner that is appealing. Common flavorings favored by equines include, but are not limited to apple, peppermint, or citrus flavors.

In particular embodiments, a chitosan composition described herein comprises one or more fruits, vegetables, herbs, or other plant-based compositions. Advantageously, such fruits, vegetables, and herbs have antioxidant or anti-inflammatory properties. In one particular embodiment, a chitosan composition comprises a plant-based pomace. Pomace is the pulpy residue that remains after the plant materials have been pressed or crushed to extract its juice. Fruits, vegetables, herbs, and plants may be provided in the form of pomace, such as a powder, liquid, solid or concentrated form based on the whole or a part of the flora. Common examples of pomace include, but are not limited to, apple powder, beet powder, beetroot powder, banana or banana peel powder, and compositions from berries (for example, blueberry, blackberry, raspberry, strawberry, cranberry).

In particular embodiments, a chitosan composition described herein comprises a polyol, including but not limited to glycerol, glycerine, or glycerin, maltitol, sorbitol, xylitol, erithritol, or isomalt, which are a group of sugar alchohols that may be used to provide sweetening while maintaining moisture content in the resulting solution. In one embodiment, one or more polyols are added to a composition of the invention to maintain the moisture of the composition, binding the nutraceutical composition in paste form for optimum ingredient activity, while additionally affecting the flavor profile.

The resulting solution, which may vary in viscosity, may in another embodiment have a nano-particulate dispersed within the solution. Nano-particulate silver and nano-particulate magnesium may be used to prevent bacterial, microbial, or fungal contamination of the solution itself or in the treated local environment. Further nano-particulate metals and non-metals have been shown to interact at the cellular level, which may have a preservative, or active pharmaceutical or medicinal effect. Bioactive ingredients, such as bioactive metals (e.g., Copper, Arsenic, Zinc, Tellurium, Mercury) in varying size ranges may also be added.

In one embodiment, the invention provides a composition comprising chitosan and manuka honey in any proportion (e.g., 0.5:10, 1:10, 2:20, 3:10, 4:10, 5:10, 6:10, 7:10, 8:10, 9:10, 10:0.5, 10:1, 10:2, 10:3, 10:4, 10:5, 10:6, 10:7, 10:8, 10:9, 1:1), further characterized by the addition of one or more of the following:
  Slippery elm (dried elm powder),
  Inulin as a probiotic,
  Ascorbic, citric, and malic acids,
  Lecithin,
  Apple Pectin,
  Apple (powder)
  Beetroot (powder)
  Potassium Sorbate (as a preservative)
  Aloe Vera
  Glycerin
Pharmaceutical and Nutraceutical Formulations
In one embodiment, a composition of the invention for use in treating or preventing ulcers is a paste or a gel composition. Admixed and/or otherwise associated or combined with the gel or paste phase is one or more healing agents formulated for oral administration. By way of example, a composition of the invention is formulated for oral or buccal administration, including, without limitation, roof of mouth, dental, periodontal, or esophageal administration. In particular embodiments, food source (animal feed), nutrition source, libation source, or food and/or drink supplement could be used. In an embodiment, the combination product could be provided in an aqueous formulation, administered to the animal as a drench or directly from a ready-to-use (RTU) bottle directed to the esophageal cavity. In a related embodiment, administration can also be by inclusion in the regular or special diet of the animal, such as in a functional food for the animals in need, or as a dietary supplement or food supplement for administration to an animal in need thereof according to the present invention.

Nonlimiting examples of suitable carriers, excipients, diluents and vehicles include lactose, dextrose, sucrose, sorbitol, mannitol, starches, gum acacia, calcium phosphate, alginates, calcium silicate, microcrystalline cellulose, polyvinylpyrrolidone, cellulose, collagen, gelatin, syrup, methyl cellulose, methyl- and propylhydroxybenzoates, talc, magnesium, stearate, water, mineral oil, edible oils, and the like. In particular embodiments, the carrier is a juice or water (e.g., coconut water, aloe water). The formulations can also include lubricating agents, wetting agents, emulsifying and suspending agents, preserving agents, sweetening agents or flavoring agents.

Formulations of the invention include ranges of the following ingredients in

TABLE 1

| Ingredient | Percentage |
| --- | --- |
| Water | 25-40 |
| Aloe Water | 25-40 |
| Apple Butter | 15-40 |
| Apple Pectin | 1-15 |
| Lecithin | 1-15 |
| Xylitol | 1-15 |
| Inulin | 1-15 |
| Glycerin | 1-15 |
| Manuka honey | 1-10 |
| Malic acid | 1-10 |
| Chitosan | 1-10 |
| Ascorbic acid | 0.1-1.0 |
| Slippery Elm | 0.1-1.0 |
| Citric acid | 0.1-1.0 |
| Potassium sorbate | 0.01 |
| Apple powder/flavoring | 10-30 |
| Sorbitol | 1-10 |
| Beet root powder | 1-10 |
| Hyaluronic acid | 1-25 |
| schizophyllan | 1-10 |

The compositions of the invention are administered, for example, on a daily basis. The amount administered can range from about 1 to about 10 mg/kg/day once, twice or more daily; or from about 1 to about 5 mg/kg/day, from about 1 to about 8 mg/kg/day, from about 1 to about 10 mg/kg/day, or from about 2 to about 4 mg/kg/day once, twice or more daily. In other embodiments, a composition of the invention is administered, for example, twice daily, three times daily, four times daily, or more than four times daily. The amount of the composition administered will vary with the weight of the animals. A foal, which weighs about 50 kg would receive about 1, 3, 5 or 10 g of a composition of the invention per day, i.e., about 1 g/50 kg, 3 g/50 kg, 1 g/10 kg, or 1 g/5 kg per day. In contrast, a full grown horse weighing 500 kg, might receive up to 80 kg per day (i.e., 1 g/25 kg, 2 g/25 kg, 3 g/25 kg, 4 g/25 kg, 1 g/5 kg, 10 g/25 kg, 20 g/25 kg.)

Doses administered once or multiple times per day can be given for consecutive days, e.g., two days, three days, four days, five days, six, days, seven days, or more, in some embodiments. A dose administered multiple times per day may embrace two, three, four, five, six, ten, or more times per day. Other dosing schedules, such as every other day, or every third day, every fourth day, etc. are embraced by the invention. In addition, one having skill in the art will appreciate that doses and amounts administered to the animal can vary, given the wide range of weights of the animals undergoing treatment, as well as the animal species and type of digestive system, e.g., ruminant or non-ruminant.

Methods of Use

The invention is directed to methods of treating and preventing ulcers of the gastrointestinal region in young and adult animals, particularly equine animals, such as horses that can be naturally high-strung and can become stressed as a result of events in their habitats and lifestyles, as well as from endurance activities and performances expected of them. The method of the invention comprises administering to an animal in need of ulcer treatment or prevention. Treating the ulcers can also involve decreasing the discomfort and pain associated with ulceratic lesions in the animal undergoing treatment.

The non-human young and adult animals for which the treatment methods are suitable may include different animal types, genera, or species. In general, young and adult farm animals, animals bred or kept for various purposes, such as sport (e.g., racing, riding, dressage), transport, domestic, companion (e.g., dogs, cats), industrial uses (e.g. hauling, pulling, plowing), and the like, are particularly amenable to treatment according to the methods of the invention. For example, encompassed by the methods of the invention is the treatment of adult or young non-human animals, such as camels (calves), sheep (lambs), rams, horses (foals), pigs (piglets), goats (kids), bison/buffalo (calves), llamas, donkeys, mules, yaks, etc. Neonatal, young and adult exotic animals, such as zoo animals of various species, are also embraced by the treatments of the invention. In preferred aspects, young and adult horses are animal subjects that are particularly amenable to the methods and compositions of the invention.

Example 1: Formula 1

A paste for oral delivery to an equine was produced. The paste contained the following materials:
Apple powder/flavoring . . . 17.22%
Water/aloe water . . . 53.2% (50/50 split)
Lecithin . . . 6.24%
Apple pectin . . . 4.48%
Sorbitol . . . 4.15%
Glycerin . . . 2.97%
Manuka honey . . . 2.2%
Beet root powder . . . 2.2%
Inulin . . . 2.02%
Malic acid . . . 2.02%
Chitosan . . . 1.65%
Slippery elm . . . 0.81%
Ascorbic acid . . . 0.37%
Citric acid . . . 0.26%
Potassium sorbate . . . 0.15%

Under a veterinarian's supervision, the formulation was administered to race horses in training suffering from ulcers. An improvement in the horse's physical performance was observed, indicating that the administration had been effective in ameliorating symptoms associated with the presence of ulcers. In at least one horse, an improvement in hind gut ulcers was observed using the Succeed Equine Fecal Blood Test™, which measures albumin and hemoglobin as indicators of gastrointestinal injury.

Example 2: Formulation 2

A composition for delivery to an equine was produced. The composition contained the following materials:
Water/Aloe Water (50/50 ratio)—37.6%
Apple Butter—29.1%
Apple Pectin—7.49%
Lecithin—7.07%
Xylitol—4.58%
Inulin—3.33%
Glycerin—3.33%
Manuka honey—2.5%
Malic acid—2.12%
Chitosan—1.87%
Ascorbic acid—0.42%
Slippery Elm—0.42%
Citric acid—0.25%
Potassium sorbate—0.08%

Under a veterinarian's supervision, the formulation was administered to horses suffering from ulcers.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for treating a gastric ulcer in an animal in need thereof, the method comprising administering to the animal a therapeutically effective amount of a composition comprising dried elm powder (*Ulmus rubra*) and a biopolymer selected from the group consisting of chitosan, cellulose, collagen, and alginate.

2. The method of claim 1, wherein the animal is an equine, bovine, ovine, feline, or canine animal.

3. The method of claim 1, wherein the chitosan is present in the range of 0.00001 to 10 wt %, from 0.00001 to 5 wt %, or from 0.00001 to 3 wt %; and wherein the dried elm powder is present in the range of from 0.1 to 1 wt %.

4. The method of claim 1, wherein the composition is formed into a powder, feed, feed additive, or treat.

5. The method of claim 1, wherein the animal has Equine Gastric Ulcer Syndrome (EGUS).

\* \* \* \* \*